United States Patent
Gvozdic et al.

(10) Patent No.: US 6,197,034 B1
(45) Date of Patent: Mar. 6, 2001

(54) MEDICAL MARKING DEVICES AND METHODS FOR THEIR USE

(76) Inventors: Nedeljko Vladimira Gvozdic, 13709 Progress Blvd. Box 8, Alachua, FL (US) 32615; Farrel LeVasseur, 2070 Reppuhn, Bay City, MI (US) 48706

( * ) Notice: Subject to any disclaimer, the term of this patent is extended or adjusted under 35 U.S.C. 154(b) by 0 days.

(21) Appl. No.: 09/326,386

(22) Filed: Jun. 4, 1999

(51) Int. Cl.[7] .................................................. A61B 17/34
(52) U.S. Cl. .......................................... 606/116; 606/185
(58) Field of Search .................................... 606/116, 185, 606/186; 81/9.22; 401/5, 105, 115

(56) References Cited

U.S. PATENT DOCUMENTS

| | | |
|---|---|---|
| 2,630,593 * 3/1953 | Jockers | 401/115 |
| 3,159,863 * 12/1964 | Mura | 401/101 |
| 4,031,783 * 6/1977 | Paul et al. | 81/9.22 |
| 4,508,106 4/1985 | Angres . | |
| 4,582,060 * 4/1986 | Bailey | 606/186 |
| 4,665,912 5/1987 | Burton . | |
| 4,671,277 6/1987 | Beuchat . | |
| 4,719,825 1/1988 | Lahaye . | |
| 4,838,722 * 6/1989 | Katz | 401/101 |
| 4,914,988 * 4/1990 | Chang | 81/9.22 |
| 5,472,449 * 12/1995 | Chou | 606/186 |
| 5,496,304 3/1996 | Chasen . | |
| 5,776,158 * 7/1998 | Chou | 606/186 |
| 5,810,862 9/1998 | Pilmanis . | |
| 5,853,366 * 12/1998 | Dowlathshahi | 600/434 |
| 5,951,185 * 9/1999 | Kingsford et al. | 401/99 |
| 6,033,421 * 3/2000 | Theiss et al. | 606/186 |

* cited by examiner

Primary Examiner—Gene Mancene
Assistant Examiner—Michael B. Priddy
(74) Attorney, Agent, or Firm—Robert L. McKellar

(57) ABSTRACT

The invention disclosed herein deals with a medical marking device which is useful for making lines and marks on soft and hard tissue of a mammal. The invention also deals with a pen containing a medical marking device and methods of using such pens to make lines and marks on soft and hard tissue of a mammal. The pen, which can be used for surgical or any other medical marking applications, is configured to be held freely in a person's hand like an ordinary writing instrument.

10 Claims, 3 Drawing Sheets

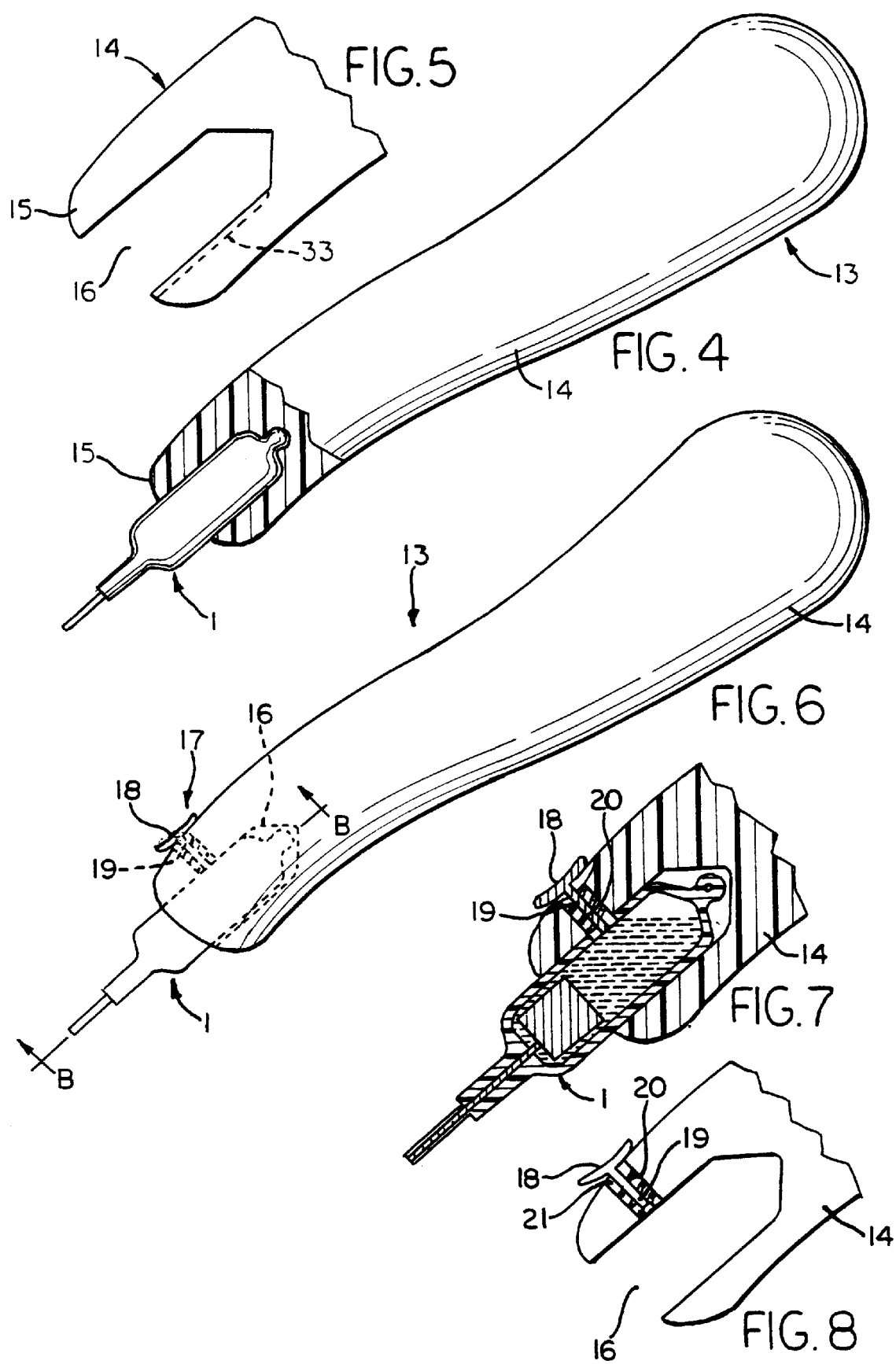

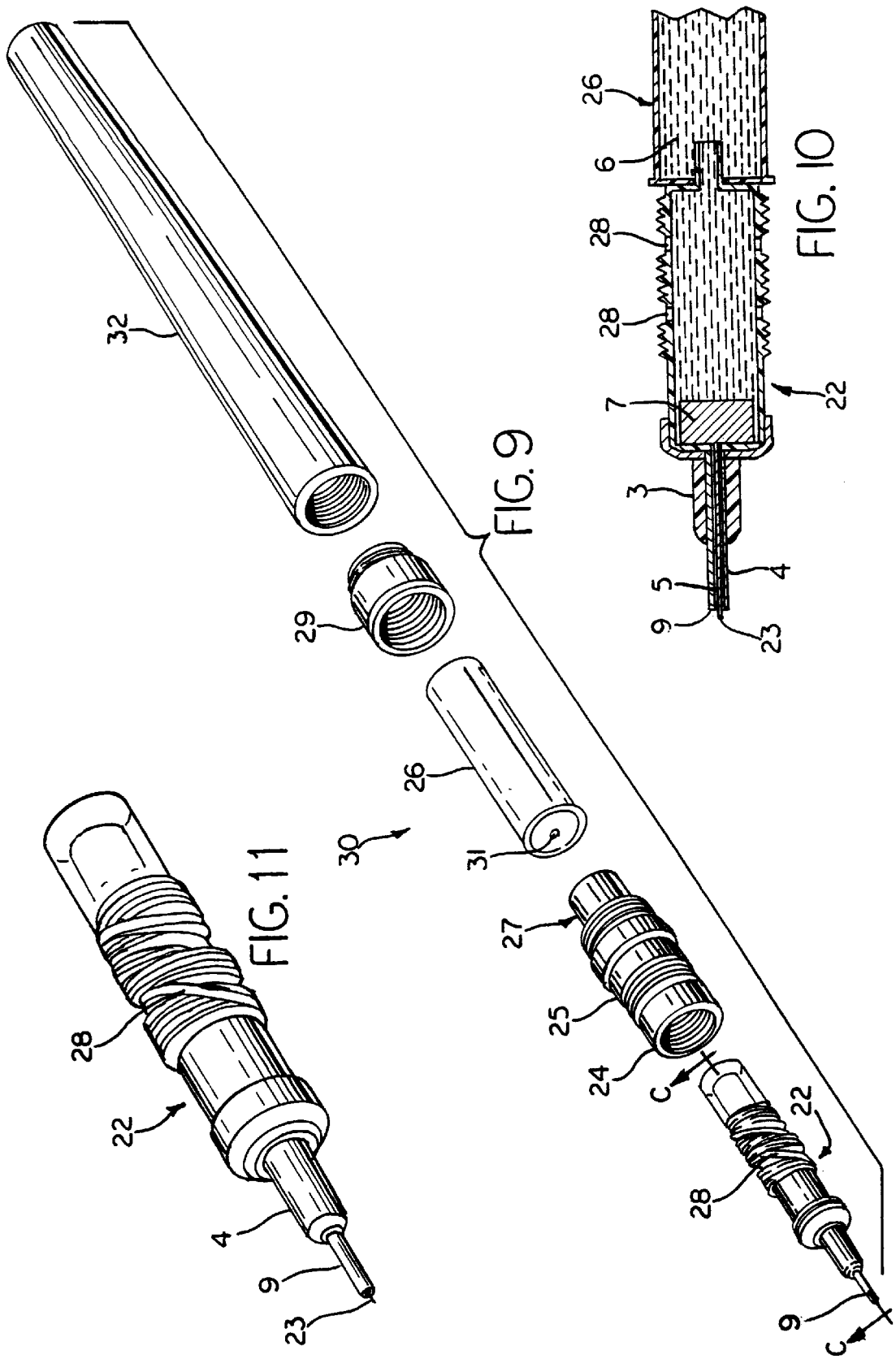

MEDICAL MARKING DEVICES AND METHODS FOR THEIR USE

TO WHOM IT MAY CONCERN

Be it known that We, Nedeljko Vladimira Gvozdic, a resident of the County of Alachua, City of Gainesville, State of Florida, and Farrel LeVasseur, a resident of the County of Bay, City of Bay City, State of Michigan, both Citizens of the United States, have invented new and useful devices which are

MEDICAL MARKING DEVICES AND METHODS FOR THEIR USE

The following of which is a specification therefor.

The invention disclosed and discussed herein deals with a medical marking device which is useful for making lines and marks on soft and hard tissue of a mammal. The invention also deals with a pen containing a medical marking device and methods of using such pens to make lines and marks on soft and hard tissue of a mammal. The pen, which can be used for surgical or any other medical marking applications, is configured to be held freely in a person's hand like an ordinary writing instrument.

BACKGROUND OF THE INVENTION

The invention deals with a medical marking device which is useful for making lines and marks on soft and hard tissue in preparation for surgery or other medical applications in which medical personnel are required to draw lines of different widths or colors or, to make reference points on the surface or under the surface of the skin or other appropriate hard and soft tissues of a body.

It is known to those skilled in the art that a number of medical procedures require the placement of various types of lines and dot-type markings on the surface of tissue or, the placement of reference points just under the surface of the tissue.

Furthermore, it is known to those skilled in the art that surgeons need to draw lines on the surfaces of hard and soft tissue of the body before surgery, to mark the position of the incision line. A surgeon needs to make these markings on tissue such that the lines can be easily drawn with desirable and consistent line widths. Also, the markings sometimes need to vary in color. These lines and marks need to be drawn with precision, and in the case of the dots, the surgeon may use the dots to do a surgical outline, but then must be able to connect the dots, and thus, the surgeon must be able to see the dots and draw the connecting line with precision. Such demands are even greater when small children are subjected to corrective surgery. The younger the child, the more precise the surgical treatment has to be in order for a scar from such surgery to be less visible after the healing process.

Serious obstacles have been created, particularly for reconstructive surgeons by the unavailability of a device which a surgeon can use to precisely and preferably "on demand" place reference points just under the surface of the skin or other body tissues. When placed just under the surface of tissues, these reference marks remain visible only temporarily in such tissues. In addition, the device must be capable of being sterilized before use.

The reference points are placed by the surgeon prior to surgical procedures. Once the surgical procedure has started, body fluids may smear the original lines when the fluids are being wiped off the body, and the original lines may become completely erased. As indicated supra, precise redrawing of original lines is possible only if a surgeon can place these multiple reference points into the tissue along the path of the line and redraw lines between these reference points. Placement of the reference points is a tedious and hard task. The precision and ease by which surgeons can place these reference points to a large extent determines how precisely the surgeon can carry out complicated reconstructive and corrective surgery. The more precise a surgeon can carry out the surgical procedure, the more likely after the healing process the patient will have minimized visibility of the surgical scar and the more likely the body tissue will be reconstructed in a proper manner.

Some of today's surgeons do not make reference points at all since there is no really good commercially available device to make such points.

Currently available, and mostly used surgical marking devices for drawing lines on the surface of a tissue are felt-tipped or fiber-tipped. These devices are identical in construction to ordinary writing felt tip or fiber tip pens. In surgical applications, such pens are sterilized and filled with appropriate FDA approved ink or coloring agents. These commercially available pens draw lines reasonably well on dry skin, however, when the skin is wet, such as by fluids, such as, for example, saline, blood, and the like, they absorb these fluids and cease leaving lines and/or marks. Consequently, surgeons have to use more than one of these pens during a single surgery, especially if they have to re-draw the lines. Currently, commercially available pens are not only cost ineffective choices, with no alternatives, but more importantly, the unreliable and unpredictable performance of these pens frustrates most of the surgeons, especially those doing intricate surgical procedures.

Some surgeons refuse to use existing commercially available pens and they use their own home made devices which are not only inconvenient to use, but may endanger the patient, because such devices cannot always be adequately sterilized. Another disadvantage of using currently commercially available surgical grade felt and fiber tip based pens is the difficulty in controlling line width. The width of lines is often unpredictable depending on the angle under which the pen is used for drawing, on the softness of felt used in the felt tip pens, and the pressure that the surgeon exerts on the pen while drawing on the surface of the tissue. The line width becomes, to a large extent, an arbitrary and difficult to control process, since the width can change during the drawing of a single line. Line width cannot be precisely predetermined. This is particularly the case when a surgeon writes on the surface of a wet body tissue. Marks are typically wider than the intended incision, for example in the repair of a cleft lip, complicating the surgical procedure and restricting precision of the corrective surgery.

The "home made" procedure identified above can be found essentially in U.S. Pat. No. 4,508,106, which issued Apr. 2, 1985 to Angres, in which the eye lid is anesthetized and stabilized, and a series of needles coated with pigment solution is inserted into the edge of the eye lid to implant the pigment solution into the dermal and/or epidermal layer of skin beneath the eye lid edge.

There is disclosed in U.S. Pat. No. 4,665,912, which issued May 19, 1987 to Burton, a device which operates in a similar manner to a ball point pen configuration, but with the modification that the tubular barrel has a narrow opening at one end, and there is a needle carried in the barrel which can extend out of the barrel. The needle and opening form an annular flow passage for a dye carried in a reservoir. The device can move the needle in and out of the opening by an internal device which extends and retracts the needle and in the process, provides the dye onto, or into the skin. It should be noted that the internal device is spring loaded to manually move a tapered needle. It requires the dye to have a viscosity substantially higher than water. Pens used for tattooing require that the dye have a viscosity substantially greater than that of water. In the instant invention, the preferred viscosity of the dye/ink is actually the viscosity of water, even though the viscosity of the dye/ink can be higher or lower than that of water. Thus, this device is substantially different from the devices of the present invention.

U.S. Pat. No. 4,671,277, which issued on Jun. 9, 1987 to Beuchat deals with a device for controlling the dispensing of pigments in solution by the use of a reciprocating needle. This device is driven by a motor and is the typical "tattoo" pen.

Yet another tattoo device can be found in U.S. Pat. No. 4,719,825, which issued on Jan. 19, 1988 in which the tattooing device includes a disposable syringe in which a tattoo dye is dispensed through a passageway in a needle of the syringe. A cam member is rotated to rotate a clutch rod held in a clutch member. The clutch rod rotates a threaded rod through a fixed nut member that causes the threaded rod to move linearly towards the syringe to displace a plunger pin fixed to the threaded rod. The plunger pin thereby displaces a plunger of the syringe to dispense the tattoo dye through the needle.

A surgical marking pen is disclosed in U.S. Pat. No. 5,496,304, which issued on Mar. 5, 1996 to Chasan, in which there is disclosed an apparatus for penetrating the epidermis. It provides for the delivery of a marking agent from a reservoir to the skin by pressure on the reservoir.

Finally, there is disclosed in U.S. Pat. No. 5,810,862, an instrument for the intradermal injection of pigments, which patent issued on Sep. 22, 1998 to Pilmanis, in which a there is an elongated tubular barrel member and a tubular grip member which is mounted at the forward end of the barrel member in coaxial relationship. The needle assembly is inserted into the barrel member in a manner such that the free ends of the individual needles project through the forward end of the grip member. A resilient member is provided within the tubular member for biasing the needle assembly toward the forward end of the grip member so that the free ends of the needles will project out through the forward end of the grip member.

Although the U.S. patent literature discloses surgical marking tools, there appears to be commercially available, only felt tipped and fiber tipped based pens for surgical use. The U.S. patent literature discussed above discloses other marking approaches, such as ball point pens, roller point pens, multiple needles, and the like. These technologies suffer from a lack of ability to draw narrow lines and lack the ability to provide preciseness and cannot generally be used to make a reference point under the surface of a tissue that will remain visible.

None of the devices of the prior art show or describe the devices of the instant invention, and none of the devices of the prior art have the advantages of the devices of the instant invention, which will be described infra.

THE INVENTION

The invention disclosed and discussed herein deals with a medical marking device which is useful for making lines and marks on soft and hard tissue of a mammal. The invention also deals with a pen containing a medical marking device and methods of using such pens to make lines and marks on soft and hard tissue of a mammal.

Thus, one objective of the instant invention is to provide a medical marking device which can serve to draw a line on the surface of a body tissue of a desired thickness or width, and of the desired color, and have the ability to place reference points on the surface or just under the surface of the skin or other hard or soft body tissues.

Another objective of this invention is to provide a medical marking pen which can be used for surgical or other medical marking application which is intended to be held freely in a person's hand similar to an ordinary writing instrument.

A further objective of this invention is to provide medical personnel with an ergonomically configured lightweight device which can easily be used and which provides the surgeon or medical personnel with desired precision and the ease to draw lines, and place reference points on the tissue before the surgical procedure is performed on that tissue. Such configuration is intended to provide stability, reproducibility and precision when drawing lines and placing such reference points.

Still further, another objective of the invention is to provide a single marking device which can be used repeatedly through the surgery without loosing the ability to mark or place reference points when original lines and points become smeared by water, saline, blood or other fluids.

And further, another objective of the invention is to provide a simple surgical marking device which can easily be sterilized and which can be disposed of after use.

Yet another objective of this invention is to provide a device which can provide a marking ink or pigment on demand.

Thus, more specifically, one embodiment of this invention deals with a medical marking device comprising a housing. The housing has a hollow interior and two ends, one end of which is closed and the opposite end has an extended member located on it.

The extended member has a channel located in it, and it has attached to the end distal to the housing, a hollow tube, wherein the hollow tube and channel are co-axially aligned. The hollow tube has an interior wall and has an end distal to the extended member. The channel provides a communicative opening from the interior of the housing to the hollow tube.

The housing contains a weight inside of it, the weight having a bottom wherein there is securely attached to the bottom, a post, the post extending through the communicative opening and extending to the distal end of the hollow tube. Further, the post has a slidable, close fit to the interior wall of the hollow tube. The weight is freely movable in a vertical motion within the housing upon a vertical shaking motion being applied to the medical marking device.

The invention further includes a pen for medical marking, wherein the pen is comprised of a handle and a medical marking device as set forth just supra. The handle is provided with a notch in one end to accommodate the insertion of the medical marking device into the notch, such that it is readily detachable. The handles of the instant invention can be configured to have a special design in the notch which will aid in the insertion of the marking device, and removable of the marking device. For example, the notch need not necessarily be square in configuration, it can be hexagonal, round, triangular, or it can have any unsymmetrical shape, without detracting from the essence of this invention.

A further aspect of the invention is a method of marking soft and hard tissue of a mammal. The method comprises (I) utilizing a medical marking pen as set forth just above and (II) applying the pen to the surface of tissue, and then (III) drawing the pen across the tissue and allowing the medical ink to color the tissue.

In addition, there is another embodiment of this invention which is a method of marking soft and hard tissue of a mammal, the method comprising (A) utilizing a medical marking pen as set forth just above, (B) applying the pen to the surface of the tissue; (C) puncturing the tissue with the hollow tube and, (D) allowing the medical ink to color the surface beneath the tissue at the location of the puncture.

Yet another aspect of this invention is the use of another style of pen in a similar method, the method comprising (i) utilizing a marking pen comprising a nib containing a hollow needle point capable of delivering medical ink. The nib is insertable in one end of a hollow pen body and there is an ink reservoir insertable in the opposite end of the hollow pen body.

The nib comprises a means of allowing air to move from the nib to an ink reservoir, wherein the ink reservoir is attached to the pen body by a detachable attaching means. The ink reservoir has an opening for delivering medical ink from the reservoir to the nib.

There is also a handle for holding the pen body, the ink reservoir, and the fastening means. The medical ink is delivered from the ink reservoir to the nib and, simultaneously, air displaces the ink that moves from the ink reservoir to the nib.

Thereafter, (ii), applying the pen to the surface of the tissue and (iii), drawing the pen across the tissue and allowing the medical ink to color the tissue.

Yet, there is another embodiment of this invention which is the use of a medical marking device containing multiple color reservoirs and ink delivery tubes with posts, which reservoirs have mechanisms for actuating one color at a time. Such commercial marking devices having multi-colored ink supplies and mechanisms for actuating one color at a time are available and are useful in the instant invention.

Finally, there is one more aspect of this invention which is a method of marking soft and hard tissue of a mammal the method comprising utilizing a marking pen comprising the method as set forth just above, in the following manner: applying the pen to the surface of the tissue; puncturing the tissue with the hollow tube; allowing the medical ink to color the surface beneath the tissue at the location of the puncture.

It is contemplated within the scope of this invention to utilize any reasonably sized reservoir for holding and delivering ink. Such reservoirs can be hard case, semi-hard case, or flexible. In addition to the specific mechanisms described herein, it is contemplated that the reservoirs can be equipped with a valve arrangement which would allow for the delivery of ink or dye, with the concommensurate replacement of the ink or dye by air, but would not allow for the ink or dye to leak from the pen. It is further contemplated within the scope of this invention that a porous plug inserted into the wall of the reservoir at the end of the reservoir opposite the delivery end can act as a simple valve as described supra.

BRIEF DESCRIPTION OF THE DRAWINGS

FIG. 4 is a full view of a pen of this invention

FIG. 5 is a partial view of the tip end of the handle 14 of the pen 13 of FIG. 4, showing a simple notch configuration.

FIG. 6 is a full view of another embodiment of this invention which is a marking pen in which there is shown an ink dispensing device which provides ink "on demand".

FIG. 7 is a partial view of the tip of the pen of FIG. 6, wherein the dispensing device and the marking device are shown in cross-section from the line B—B of FIG. 6.

FIG. 8 is a partial view of a notch in the tip of the pen of FIG. 6, showing the dispensing device and one ink "delivery on demand" mechanism, with more clarity.

FIG. 9 is a break away view of a pen that is useful in the methods of this invention.

FIG. 10 is a cross-sectional view of the nib taken through the line C—C of FIG. 9.

FIG. 11 is a full view of another embodiment of the nib of FIG. 9 showing one configuration of the air channel on the outside of the barrel of the nib.

DETAILED DESCRIPTION OF THE DRAWINGS

Figure 1:
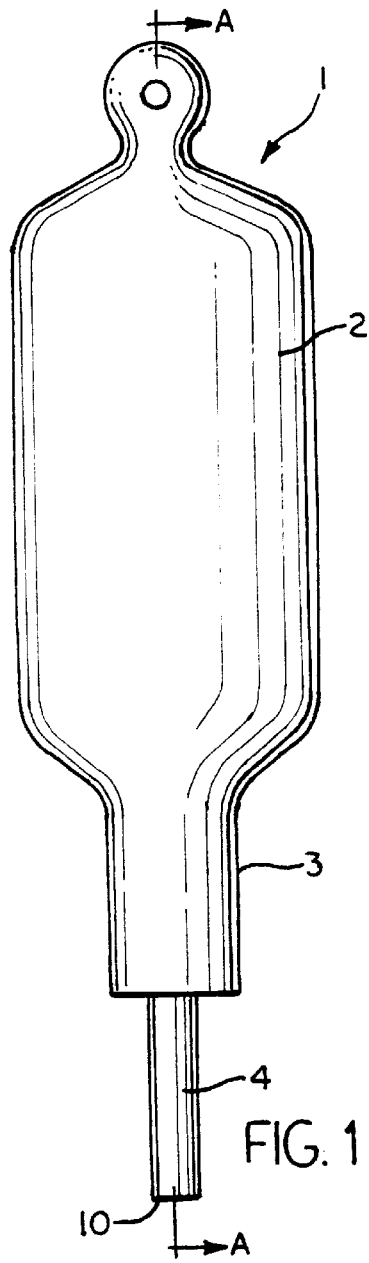
FIG. 1 is a full view of a marking device of this invention.

Turning now to FIG. 1, which is a full view of a marking device 1 of this invention wherein there is shown a housing 2 which has an integrally extended member 3, and a hollow tube 4, wherein the extended member 3 and the hollow tube 4 are coaxially aligned with each other.

Figure 2:
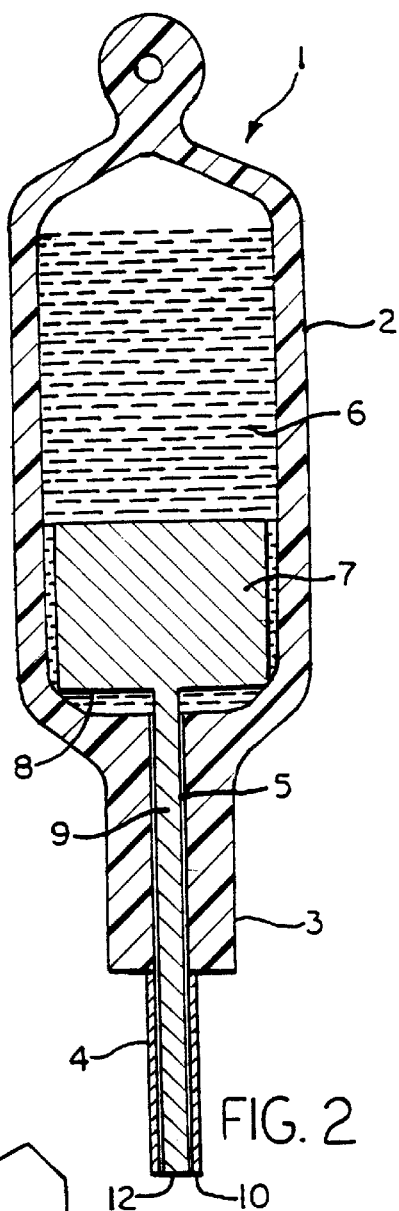
FIG. 2 is a cross-sectional full view of the device of FIG. 1, through the line A—A.

It can be observed from FIG. 2, which is a cross-sectional view of FIG. 1 at the line A—A of FIG. 1, that the housing 2 is hollow and that it has a channel 5 located in the extended member 3, which channel 3 provides a communicative opening from the interior of the housing 2 to the hollow body 4.

Also shown in the interior of the housing 2 is a supply of ink or pigmenting solution 6. The inks 6 to be used with these marking devices 1 are biodegradable, nontoxic and are absorbable by the body, or otherwise metabolically used after a relatively short period of time. An example of such an ink which has been approved by the FDA is methylene blue.

Also located in the interior of the housing 2 is a weight 7, which has a bottom 8, and attached to the bottom 8 in a secure manner is a post 9. The post 9 can be observed to extend from the bottom 8, through the channel 5, and into the hollow tube 4. The length of the post 9 is generally the length from the bottom 8 to the distal end 10 of the hollow tube 4, however, it is contemplated within the scope of this invention that the post 9 can be shorter. The post 9 is in the form of a needle and generally, it is a fine wire supported by the walls of the channel 5. It should be noted that it is the hollow tube 4 which penetrates the skin, and the post 9 may or may not penetrate the skin. Thus, the post 9 of the instant invention does not participate in any major way in the mechanism which allows the marking device 1 to penetrate the skin when one intends to place dots under the skin. The key role of the post 9 is in the mechanism of ink delivery, particularly in controlling the flow of ink to the tip of the hollow tube 4. This is one of the key differences between the devices of this invention and tattooing devices. Tattooing pens typically use an inner tapered wire, which is typically called a needle, to penetrate the skin and deliver the ink. The inner needle is designed so as to be driven by a mechanism to reciprocate along the long axis of a barrel in order to deliver ink droplets under the skin. Tattoo pens required the formation of small droplets or beads at the tip of the pen. The droplet or bead is then propelled under the skin by the reciprocating motion of the inner needle contained inside the tubular barrel. Tattooing pens work in the "discrete mode" of ink delivery, i.e. ink dot delivery, and they are not typically designed for making continuous lines. Again, this is because their sole purpose is to deliver ink under the skin as a dot. The instant invention does not assume nor require formation of droplets or beads on the tip for its successful operation. It relies essentially on continuous supply of ink to the tip. The marking devices of the instant invention can work in both modes of operation, continuous and ink dot, i.e., in a discreet mode when also equipped with a mechanism for on demand ink delivery. Dots under the skin are made by the surgeon thrusting the hollow tube of the marking device of this invention under the skin and delivering ink every time the surgeon penetrates the skin. In order to deliver the ink under the skin in a consistent manner, the depth of hollow tube 4 penetration will be limited by the length of the hollow tube 4, the hollow tube 4 is relatively short when marking is preferentially used for the creation of dots. When marking is preferentially used for line drawing, the there is essentially no limitation on how long the hollow tube 4 can be, it being within reasonable limits such that the maximum efficiency of the marking device is obtained.

Figure 3:
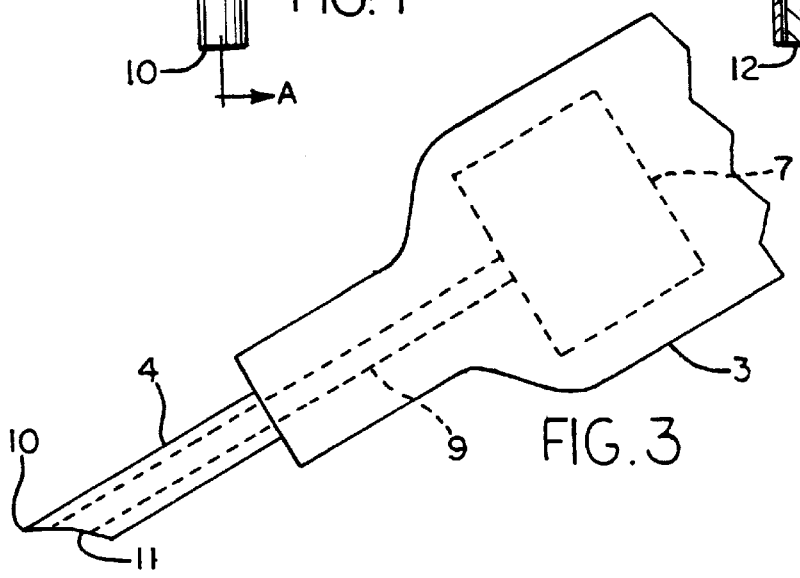
FIG. 3 is a partial view of the tip of the marking device, showing a hollow 45° cut on the hollow tube.

Although the distal end 10 of the hollow tube 4 is shown in FIGS. 1 and 2 as having a flat, 90° angle, it is further contemplated within the scope of this invention that the hollow tube 4 can have a concavity formed in its distal end 10 in order to hold more ink 6 and to provide a means of penetrating the tissue. (see FIG. 3 where the distal end 10 has a 45° angle 11 cut into it and the weight 7, and the post 9, are shown in phantom). Thus, there is provided for in this invention for an angle to be cut into the distal end 10 of the hollow tube 4 at any angle from about 20° to 90°, with the preferred angles being between about 35° and 90°, and the most preferred angles being from about 45° to 90°, and it is further contemplated within the scope of this invention that such angles can be cut with a concavity configuration. Thus, it is further contemplated within the scope of this invention that the hollow tube 4 can have a concavity formed in its distal end 10 in order to hold more ink 6 and to provide a means of penetrating the tissue. This will ensure that a sufficient volume of ink is delivered to the point under the skin. If the marking device is used preferentially to write on the surface of a tissue, the preferred angle of the cut of the end of the tube is 90°. If the pen is preferentially used for delivery of ink just under the surface of a tissue, the preferred cut of the end of the tube is less than 90°. This will ensure penetration of the ink into the skin. Generally, all commercial pens have a cut of 90° and do not provide for any lesser angle.

The post 9 must have a slidable close fit within the channel 5 in order for the ink 6 to be able to reach the end of the hollow tube 4. By "slidable close fit" it is meant for purposes of this invention that the post 9 should be freely moveable within the channel 5 to enable it to slide up and down with the weight 7, but it should not have continuous contact with the interior walls of the channel 5 that causes undue friction. Further, there must be room between the post 9, and the interior walls of the channel 5 and the hollow tube 4 for the ink 6, and to ensure that ink flow to the point of the hollow tube 4 is not inhibited. This "room" is such that the ink is held, and moves, in the channel 5 and the hollow tube 4. In this manner, when the marking device 1 requires re-inking, or if the tip of the hollow tube 4 is blocked, then the marking device 1 is shaken in a vertical motion, the weight 7 and the post 9 move together. As the post 9 moves up the channel 5 and moves down the channel 5, it helps bring a new supply of ink 6. It should be understood by those skilled in the art that capillary action alone will not provide for the transfer of the ink 6 from the housing 2 in a consistent and reliable manner if the hollow tube 4 is used alone without the post 9, and that the combination of the weight 7 and the post 9 are required to deliver the ink 6 in a continuous, even and smooth manner, especially for the restoration of the marking ability of the device, by re-inking the tip.

Furthermore, the return of the distal end 12 of the post 9, clears the end of the hollow tube 4 from any debris or fluids that have come in contact with the hollow tube 4. Since in our Figure, the housing 2 is flexible, it collapses inwardly as the ink 6 is removed, owing to the fact that there is no air supplied to the interior of the housing 2 in this particular device, and as the ink 6 leaves the housing 2, it creates a slightly negative pressure which causes the collapse of the housing 2. Upon touching the distal ends 10 and 12 to the tissue, the ink 6 moves to the tissue in a continuous, even and smooth flow. This manner of providing the ink 6 allows for a non-leaking device and a convenient way to re-ink the tip of the marking device. Thus, the role of the post 9 in the hollow tube 4 is to control the flow of the ink; prevent uncontrolled flow of the ink down the hollow tube 4; restore marking ability of the marking device if it stops writing, and make it possible to have only one pen per surgery which will consistently and reliably write every time when needed.

Turning now to FIG. 4, which is a full view of a marking pen 13, of this invention, in which there is shown a marking device 1 and a handle 14. The marking device 1 is inserted into one end 15 of the handle 14 such that it is secure during its use, but is removable with ease for disposal of the marking device 1. There is provided a notch 16 in the end 15 of the handle for such a purpose. The notch 16 is better viewed from FIG. 5 which is an enlarged tip 15 of the handle 14 in FIG. 4. It will be recalled that the marking device 1 and the handle 14 with the notch 16 are constructed so that they fit into each other and it is contemplated within the scope of this invention that the notch can be keyed such that the marking device will only fit into the notch in one way, and further, such keying of the notch can provide for a means on holding the marking device in the notch while the marking pen is being used. Such a keyed configuration can be found in FIG. 5, where the key is shown as 33 and in phantom.

It is further contemplated within the scope of this invention to package the marking device 1 and the handle 14 separately for sterilization. It is still further contemplated within the scope of this invention to separately sterilize the marking device 1 and the handle 14 and supply them both in the same package. It is also intended within the scope of this invention that marking device 1 be either disposable or reusable, and that the handle 14 be either disposable or reusable. It should be understood by those skilled in the art that the handle 14 has an ergonomic configuration or it can have any configuration that provides for its use without hindering the task of providing lines and marks, and which further is capable of sterilization. Finally, it is contemplated within the scope of this invention that the tip of marking pen can have a cap which will allow for easy sterilization, storage, and a means of preventing the ink from drying out.

Another embodiment of this invention can be found in FIG. 6, which is a full view of a pen of this invention in which there is shown a handle 14, containing a notch 16 into which is inserted a marking device 1 of this invention. As described supra, the notch can be any configuration as long as it accommodates the insertion of the marking device therein. FIG. 5, shows another embodiment of the invention which is a groove 33, shown in phantom, into which a fin or blade which is part of the marking device 1, can be inserted to hold the marking device 1 in place in the notch 16. p Also shown is one embodiment of an ink dispensing device 17, which is a spring loaded button in the side of the handle 14, which is comprised of a depressible button 18, the button 18 having a shaft 19 (shown in phantom) connected thereto, which is surrounded by a spring 20 (see FIG. 7). The shaft 19 and the spring 20 are slidable through a channeled opening 21. FIG. 7 is a cross-sectional view of the tip end of FIG. 6, through the line B—B and FIG. 8 is a portion of the tip end of the pen from FIG. 6, in which the parts are shown with more clarity. Thus, the pen can be shaken to clear the channel 5 and the hollow tube 4 and re-ink the tip of the marking device and the button can be depressed to deliver ink through the channel 5 and the hollow tube 4 for delivery of a dot under the skin. Even so, the pen does not have to be shaken with the use of the dispensing device 17, in that, a depression of the button 18, even with the post 9 in the channel 5 and the hollow tube 4, will allow the delivery of ink 6 to the tip thereof.

Further embodiments of the "ink on demand" mechanisms are, for example, sliding or clicking mechanisms used in commercial drafting pencils to move lead or, the mechanisms which are used for delivery of microliter volumes of liquid by syringes, such as those used in gas chromatography.

It is preferred, that the aforementioned mechanisms be built into the housing of the pen such that the pens are easily sterilized.

Turning now to another embodiment in which with reference to FIG. 9 there is shown a marking pen 30 which is used in a method of marking soft and hard tissue, in which the method comprises using the pen described infra, applying the pen to the surface of the tissue, and then drawing the pen across the tissue and allowing the medical ink to color the tissue, and a secondary method of marking soft and hard tissue which comprises utilizing the same type of pen; applying the pen to the surface of the tissue; puncturing the tissue with the hollow tube, and then allowing the medical ink to color the surface beneath the tissue at the location of the puncture.

The pen indicated just supra, comprises in combination a nib 22, containing a hollow needle point 23, and a fine wire attached to the weight, capable of delivering medical ink. The nib 22 is insertable in one end 24 of a hollow pen body 25, and an ink reservoir 26 is insertable in the opposite end 27 of the hollow pen body 25.

The nib is comprised of a means 28 of allowing air to move from the nib 22 to the ink reservoir 26. The ink reservoir 26 is attached to the pen body 25 by a detachable attaching means 29. The ink reservoir 26 has an opening 31 for delivering medical ink from the reservoir 26 to the nib 22. There is in addition, a handle 32 for holding the pen body 25, the ink reservoir 26, and the attaching means 29.

The medical ink can then be delivered from the ink reservoir 26 to the nib 22, and simultaneously, air displaces the ink that moves from the reservoir 26 to the nib 22 via the means 28 which is a hollow tube on the outside surface of the nib 22.

FIG. 10 is a full cross-sectional view of the nib of FIG. 9 through the line C—C and shows the ink reservoir 26 in partial, the ink 6, the air channel 28 around the outside of the nib 22, the weight 7, the hollow needle point comprised of the post 9, hollow body 4, and extended member 3, wherein the post 9 is attached to the bottom of the weight 7 and moves with the movement of the weight 7.

FIG. 11 is a side view of the nib 22 showing another configuration of the air channel 28 around the outside of the nib 22.

It has been found that this type of pen serves very well for medical marking and has all of the advantages of the pen described above that has the collapsible ink reservoir.

Pens similar to this type of pen are commercially available and are sold under the trade name of KOH-I-NOOR and are available from most drafting equipment and supply stores.

What is claimed is:

1. A medical marking device comprising a housing, said housing having a hollow interior and said housing having two ends, one end being closed and the opposite end having an extended member located thereon;

said extended member having a channel located therein, said extended member having attached to the end distal of the housing, a hollow tube, said hollow tube being coaxially aligned with the channel and said hollow tube having an interior wall, said hollow tube having an end distal to the extended member, said channel providing a communicative opening from the interior of the housing to the hollow tube;

said housing containing therein a weight, said weight having a bottom; said weight having securely attached to the bottom, a post, said post extending through the communicative opening and extending to the distal end of the hollow tube, said post having a slidable fit to the interior wall of the hollow tube, said weight being freely movable in a vertical motion within the housing.

2. The medical marking device as claimed in claim 1 in which the housing is flexible and collapsible.

3. The medical marking device as claimed in claim 1 in which the housing is inflexible.

4. A medical marking device as claimed in claim 1 wherein the housing contains a supply of medical ink which will color soft and hard tissue of a mammal, said ink being housed in a reservoir.

5. A medical marking device as claimed in claim 1 wherein, the housing is a multiple housing and each multiple housing contains a weight and a post, and each of the housings contain therein a different colored ink, wherein the housings are capable of being activated and controlled at will by a person using the medical marking device.

6. A medical marking device as claimed in claim 4 wherein the housing has a means of providing air to the reservoir as the ink is being dispensed from the reservoir.

7. A pen for medical marking, said pen comprising a handle and the medical marking device of claim 4, the handle having a notch in one end thereof, said medical marking device being detachedly inserted in said notch.

8. A pen for medical marking as claimed in claim 7, wherein the notch is keyed to accept and hold the medical marking device.

9. A method of marking soft and hard tissue of a mammal, said method comprising (I) utilizing a medical marking pen as claimed in claim 7;

(II) applying the pen to the surface of the tissue;

(III) drawing the pen across the tissue and allowing the medical ink to color the tissue.

10. A method of marking soft and hard tissue of a mammal, said method comprising (A) utilizing a medical marking pen as claimed in claim 6;

(B) applying the pen to the surface of the tissue;

(C) puncturing the tissue with the hollow tube;

(D) allowing the medical ink to color the surface beneath the tissue at the location of the puncture.

* * * * *